(12) United States Patent
Park et al.

(10) Patent No.: US 12,290,344 B2
(45) Date of Patent: May 6, 2025

(54) APPARATUS AND METHOD FOR ESTIMATING BLOOD PRESSURE

(71) Applicant: SAMSUNG ELECTRONICS CO., LTD., Suwon-si (KR)

(72) Inventors: Chang Soon Park, Suwon-si (KR); Ui Kun Kwon, Suwon-si (KR); Young Soo Kim, Suwon-si (KR); Hye Rim Lim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 112 days.

(21) Appl. No.: 18/129,396

(22) Filed: Mar. 31, 2023

(65) Prior Publication Data

US 2024/0172945 A1    May 30, 2024

(30) Foreign Application Priority Data

Nov. 30, 2022    (KR) .................. 10-2022-0164219

(51) Int. Cl.
*A61B 5/021*    (2006.01)
*A61B 5/00*    (2006.01)
(Continued)

(52) U.S. Cl.
CPC .......... *A61B 5/02116* (2013.01); *A61B 5/029* (2013.01); *A61B 5/7239* (2013.01);
(Continued)

(58) Field of Classification Search
None
See application file for complete search history.

(56) References Cited

U.S. PATENT DOCUMENTS

| 8,282,564 B2 | 10/2012 | Parlikar et al. |
| 2013/0018272 A1 | 1/2013 | Hori |

(Continued)

FOREIGN PATENT DOCUMENTS

| JP | 5318810 B2 | 10/2013 |
| JP | 2017-136240 A | 8/2017 |

(Continued)

OTHER PUBLICATIONS

Youngzoon Yoon et al., "Nonconstrained Blood Pressure Measurement by Photoplethysmography", Journal of the Optical Society of Korea, Jun. 2006, vol. 10-Issue 2, pp. 91-95.

(Continued)

*Primary Examiner* — Joel Lamprecht
*Assistant Examiner* — Ashish S Jasani
(74) *Attorney, Agent, or Firm* — Sughrue Mion, PLLC

(57) ABSTRACT

An apparatus for estimating blood pressure may include: a photoplethysmogram (PPG) sensor configured to measure a PPG signal from a user; and a processor configured to: extract a cardiovascular feature from the PPG signal; calculate a first variation in the extracted cardiovascular feature compared to a reference cardiovascular feature measured at a reference time; determine a measurement posture of the PPG signal based on a time interval between two waveform components of the PPG signal; in response to the measurement posture corresponding to the reference posture, estimate the blood pressure based on the first variation; and in response to the measurement posture not corresponding to the reference posture, obtain a second variation by correcting the first variation; and estimate blood pressure based on the second variation.

14 Claims, 10 Drawing Sheets

(51) Int. Cl.
*A61B 5/024* (2006.01)
*A61B 5/029* (2006.01)

(52) U.S. Cl.
CPC .......... *A61B 5/7246* (2013.01); *A61B 5/7278* (2013.01); *A61B 5/02416* (2013.01)

(56) References Cited

U.S. PATENT DOCUMENTS

| | | | |
|---|---|---|---|
| 2016/0198955 A1* | 7/2016 | Fortin | A61B 5/721 600/323 |
| 2016/0206247 A1 | 7/2016 | Morland et al. | |
| 2016/0270668 A1 | 9/2016 | Gil | |
| 2017/0172431 A1 | 6/2017 | Kim et al. | |
| 2018/0020990 A1 | 1/2018 | Park et al. | |
| 2019/0209030 A1 | 7/2019 | Shimuta | |
| 2019/0343407 A1 | 11/2019 | Huijbregts et al. | |
| 2020/0275839 A1* | 9/2020 | Park | A61B 5/7225 |
| 2021/0000429 A1* | 1/2021 | Yoon | A61B 5/6843 |
| 2021/0068668 A1* | 3/2021 | Slyusarenko | A61B 5/7235 |
| 2021/0100456 A1 | 4/2021 | Park et al. | |
| 2021/0153751 A1 | 5/2021 | Gunderson et al. | |
| 2021/0177287 A1* | 6/2021 | Kwon | A61B 5/02233 |

FOREIGN PATENT DOCUMENTS

| | | |
|---|---|---|
| KR | 10-1503604 B1 | 3/2015 |
| KR | 10-2017-0073051 A | 6/2017 |
| KR | 10-2021-0075649 A | 6/2021 |

OTHER PUBLICATIONS

Sandrine C. Millasseau et al., "The Vascular Impact of Aging and Vasoactive Drugs: Comparison of Two Digital Volume Pulse Measurements", American Journal of Hypertension, Jun. 2003, vol. 16-Issue 6, pp. 467-472.

Martin C Baruch et al., "Validation of the pulse decomposition analysis algorithmusing central arterial blood pressure", Biomedical Engineering Online, Jul. 2014, vol. 13, Article No. 96, pp. 1-19.

* cited by examiner

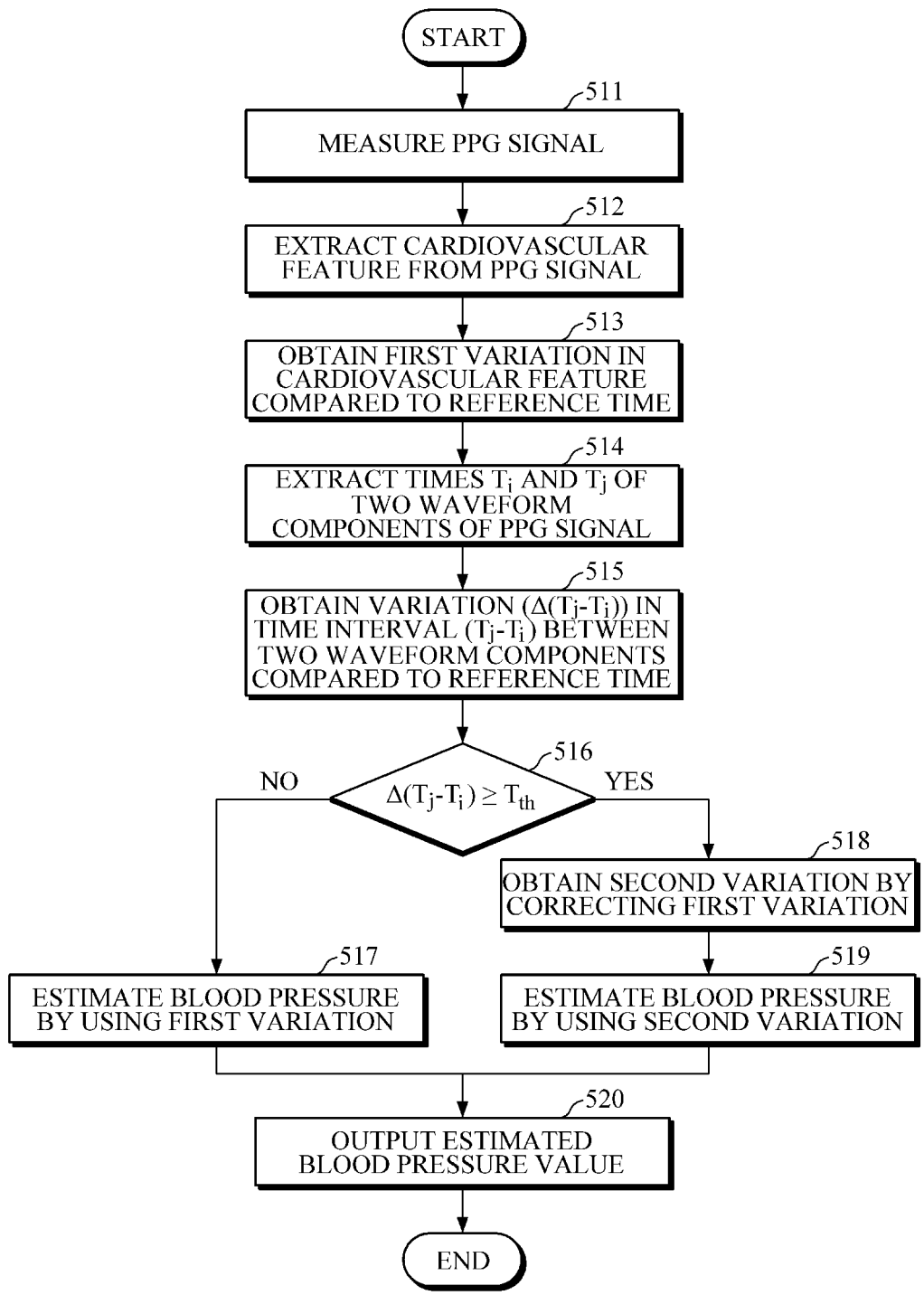

APPARATUS AND METHOD FOR ESTIMATING BLOOD PRESSURE

CROSS-REFERENCE TO RELATED APPLICATION(S)

This application claims priority from Korean Patent Application No. 10-2022-0164219, filed on Nov. 30, 2022, in the Korean Intellectual Property Office, the disclosure of which is incorporated herein by reference in its entirety.

BACKGROUND

1. Field

Apparatuses and methods consistent with example embodiments relate to estimating blood pressure by using a photoplethysmogram (PPG) signal.

2. Description of the Related Art

Research on information technology (IT)-medical convergence technology, in which IT and medical technology are combined, is being recently carried out to address the aging population structure, rapid increase in medical expenses, and shortage of specialized medical service personnel. Particularly, monitoring of the health condition of the human body is not limited to a fixed place, such as a hospital, but is expanding to a mobile healthcare sector for monitoring a user's health condition at any time and any place in daily life at home and office. Electrocardiography (ECG), photoplethysmogram (PPG), and electromyography (EMG) signals are examples of bio-signals that indicate the individual's health condition. A variety of signal sensors are being developed to measure such signals in daily life. Particularly, in the case of a PPG sensor, it is possible to estimate blood pressure of a human body by analyzing a form of pulse wave that reflects a cardiovascular state.

According to a PPG bio-signal related research, the whole PPG signal is a summation of a propagation wave propagating from the heart to peripheral parts of a body and reflection waves returning from the peripheral parts of the body. It is known that information for use in estimating blood pressure can be obtained by extracting various features associated with propagation waves or reflection waves.

SUMMARY

According to an aspect of the present disclosure, an apparatus for estimating blood pressure may include: a photoplethysmogram (PPG) sensor configured to measure a PPG signal from a user; and a processor configured to: extract a cardiovascular feature from the PPG signal; calculate a first variation in the extracted cardiovascular feature compared to a reference cardiovascular feature measured at a reference time; determine a measurement posture of the PPG signal based on a time interval between two waveform components of the PPG signal; in response to the measurement posture corresponding to the reference posture, estimate the blood pressure based on the first variation; and in response to the measurement posture not corresponding to the reference posture, obtain a second variation by correcting the first variation; and estimate blood pressure based on the second variation.

The PPG sensor may include: a light source configured to emit light to the user; and a detector configured to detect light scattered or reflected from the user.

The processor may be further configured to: obtain a variation in a difference between feature values of the two waveform components compared to a difference between feature values of two waveform components obtained at the reference time in the reference posture; and in response to the obtained variation being greater than or equal to a threshold value, determine that the measurement posture does not correspond to the reference posture.

The processor may be further configured to: obtain a second derivative signal of the PPG signal; and obtains a time of a second local minimum point of the second derivative signal, and a time of a third local minimum point of the second derivative signal, as the feature values of the two waveform components.

The processor may be further configured to obtain the second variation by subtracting a correction value from the first variation.

The processor may be further configured to calculate the correction value by multiplying an absolute value of the first variation by a predetermined coefficient.

The processor may be further configured to calculate the correction value by dividing an amplitude value of a reflection wave component of the PPG signal, measured at the reference time in the reference posture, by an amplitude value of a progressive wave component.

The cardiovascular feature may include a cardiac output (CO) feature associated with CO and a total peripheral resistance (TPR) feature associated with TPR.

The CO feature may include a ratio between a maximum amplitude value of the PPG signal and an area of a predetermined region of the PPG signal; and the TPR feature may include a ratio between an amplitude value of a first reflection wave component and an amplitude value of a progressive wave component of the PPG signal.

The processor may be further configured to: in response to the measurement posture of the PPG signal corresponding to the reference posture, combine the first variation in the CO feature and the first variation in the TPR feature, and estimate the blood pressure based on a combination of the first variation in the CO feature and the first variation in the TPR feature; and in response to the measurement posture not corresponding to the reference posture, combine the second variation in the CO feature and the second variation in the TPR feature, and estimate the blood pressure based on a combination of the second variation in the CO feature and the second variation in the TPR feature.

The processor may be further configured to: in response to the measurement posture of the PPG signal corresponding to the reference posture, estimate the blood pressure by inputting the combination of the first variation in the CO feature and the first variation in the TPR feature, and a reference blood pressure to a blood pressure estimation model; and in response to the measurement posture not corresponding to the reference posture, estimate the blood pressure by inputting the combination of the second variation in the CO feature and the second variation in the TPR feature, and the reference blood pressure to the blood pressure estimation model.

According to another aspect of the present disclosure, a method of estimating blood pressure may include: measuring a photoplethysmogram (PPG) signal from a user; extracting a cardiovascular feature from the PPG signal; calculating a first variation in the extracted cardiovascular feature compared to a reference cardiovascular feature measured at a reference time; determining a measurement posture of the PPG signal based on a time interval between two waveform components of the PPG signal; in response to the measurement posture corresponding to the reference posture, estimating the blood pressure based on the first variation; and in response to the measurement posture not corresponding to the reference posture, obtaining a second variation by correcting the first variation and estimating blood pressure based on the obtained second variation.

The determining of the measurement posture may include: obtaining a variation in a difference between feature values of the two waveform components compared to a difference between feature values of two waveform components obtained at the reference time in the reference posture; and in response to the obtained variation being greater than or equal to a threshold value, determining that the measurement posture does not correspond to the reference posture.

The determining of the measurement posture may include: obtaining a second derivative signal of the PPG signal; and obtaining a time of a second local minimum point of the second derivative signal, and a time of a third local minimum point of the second derivative signal, as the feature values of the two waveform components.

The obtaining of the second variation may include obtaining the second variation by subtracting a correction value from the first variation.

The method may further include: calculating the correction value by multiplying an absolute value of the first variation by a predetermined coefficient.

The method may further include: calculating the correction value by dividing an amplitude value of a reflection wave component of the PPG signal, measured at the reference time in the reference posture, by an amplitude value of a progressive wave component.

The cardiovascular feature may further include a cardiac output (CO) feature associated with CO and a total peripheral resistance (TPR) feature associated with TPR The CO feature may include a ratio between a maximum amplitude value of the PPG signal and an area of a predetermined region of the PPG signal; and the TPR feature may include a ratio between an amplitude value of a first reflection wave component and an amplitude value of a progressive wave component of the PPG signal.

The estimating of the blood pressure may include: in response to the measurement posture of the PPG signal corresponding to the reference posture, combining the first variation in the CO feature and the first variation in the TPR feature, and estimating the blood pressure based on a combination of the first variation in the CO feature and the first variation in the TPR feature; and in response to the measurement posture not corresponding to the reference posture, combining the second variation in the CO feature and the second variation in the TPR feature, and estimating the blood pressure based on a combination of the second variation in the CO feature and the second variation in the TPR feature.

BRIEF DESCRIPTION OF THE DRAWINGS

The above and/or other aspects will be more apparent by describing certain example embodiments, with reference to the accompanying drawings, in which:

FIG. 5 is a flowchart illustrating a method of estimating blood pressure according to an embodiment of the present disclosure.

DETAILED DESCRIPTION

Figure 1:
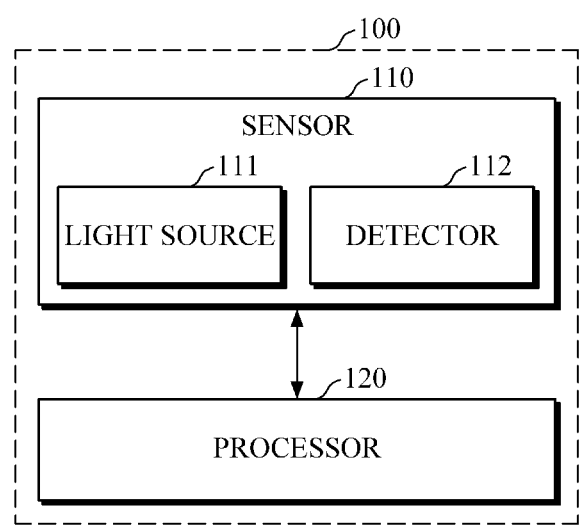
FIG. 1 is a block diagram illustrating an apparatus for estimating blood pressure according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Details of other embodiments are included in the following detailed description and drawings. Advantages and features of the present invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for estimating blood pressure according to an embodiment of the present disclosure.

Various embodiments of an apparatus for estimating blood pressure, which will be described below, may be implemented as electronic devices including a smartphone, a tablet PC, a desktop computer, a laptop computer, or various types of wearable devices, such as wristwatches, bracelets, wristbands, rings, glasses, headbands, and the like. In addition, various embodiments which will be described below may be used for estimating a variety of cardiovascular information including blood pressure, arrhythmia, vascular age, skin elasticity, skin age, arterial stiffness, aortic pressure waveform, stress index, fatigue level, and the like.

Referring to FIG. 1, an apparatus 100 for estimating blood pressure includes a sensor 110 and a processor 120.

The sensor 110 may measure a bio-signal from a body part of a user where bio-signals are easily detectable, such as a wrist skin area that is adjacent to the radial artery, or a skin area where capillary blood or venous blood passes, or a peripheral part of the body with high blood vessel density, including fingers and toes. The bio-signal may include Photoplethysmogram (PPG), Electrocardiography (ECG), Electromyography (EMG), impedance plethysmogram (IPG), Pressure wave, video plethysmogram (VPG), and other related signals. The following description will be given using a PPG signal as an example.

For example, the sensor 110 may include a light source 111 configured to emit light to an object and a detector 112 configured to detect light scattered or reflected from or transmitted into the object. The sensor 110 may measure a PPG signal from the object by using the light source 111 and the detector 112. The light source 111 may include a light emitting diode (LED), a laser diode (LD), a phosphor, and the like. The light source 111 may be formed as a single light source or an array of a plurality of light sources to emit light of one or more wavelengths (e.g., green, red, blue, and infrared wavelengths). The detector 112 may include a photo diode, a photo transistor (PTr), an image sensor (e.g., complementary metal-oxide semiconductor (CMOS) image sensor), etc., and may be formed as a single detector or an array of a plurality of detectors.

The processor 120 may be electrically or functionally connected to the sensor 110 to control the sensor 110 and to obtain a PPG signal. Under the control of the processor 120, the sensor 110 may measure the PPG signals continuously or at predetermined time intervals (e.g., one hour, two hours, four hours, etc.). The processor 120 may receive in real time the PPG signals from the sensor 110. Upon receiving the PPG signal from the sensor 110, the processor 120 may perform preprocessing on the PPG signal. For example, the processor 120 may perform signal correction, such as filtering (e.g., band-pass filtering between 0.4 Hz and 10 Hz), amplification of the PPG signal, converting the signal into a digital signal, smoothing, ensemble averaging of continuously measured PPG signals, and the like. In addition, the processor 120 may obtain a representative waveform from the entire waveform of the received PPG signal, and may estimate blood pressure by analyzing the obtained representative waveform. For example, the processor 120 may extract a representative waveform of one cycle by using a difference between lowest points in the entire waveform of the PPG signal. In this case, the processor 120 may obtain a plurality of unit waveforms of one cycle from the waveform of the PPG signal, and may obtain the representative waveform by using any one or a combination of two or more of the plurality of unit waveforms.

The processor 120 may extract a cardiovascular feature associated with blood pressure from the PPG signal and may estimate blood pressure based on the extracted cardiovascular feature.

A variation in mean arterial pressure (MAP) is proportional to cardiac output (CO) and total peripheral resistance (TPR), as shown in the following Equation 1.

$$\Delta MAP = CO \times TPR \quad \text{[Equation 1]}$$

Herein, $\Delta$MAP denotes a difference in MAP between the left ventricle and the right atrium, in which MAP of the right atrium is generally within a range of 3 mmHg to 5 mmHg, such that the MAP in the right atrium is similar to MAP in the left ventricle or MAP of the upper arm. If absolute actual CO and TPR values are known, MAP may be obtained from the aorta or the upper arm. However, it may be difficult to estimate absolute CO and TPR values based on a PPG signal.

Accordingly, the processor 120 may extract, from the PPG signal, a CO feature associated with CO or a TPR feature associated with TPR, and may estimate blood pressure by using the extracted CO feature and TPR feature. Here, the CO feature may be a feature value which shows an increasing or decreasing trend in proportion to an actual CO value which relatively increases or decreases. Further, the TPR feature may be a feature value which shows an increasing or decreasing trend in proportion to an actual TPR value which relatively increases or decreases.

The processor 120 may calculate a ratio ($P_{max}/PPG_{area}$) between a maximum amplitude value $P_{max}$ and a waveform area of the PPG signal as the CO feature. The maximum amplitude value $P_{max}$ may be an amplitude value of a point at which a slope is closest to zero in a systolic region of the PPG signal or an amplitude value corresponding to a first local minimum point in a second derivative signal of the PPG signal. The waveform area $PPG_{area}$ may be a total area under the waveform or an area of a predetermined region of the PPG signal. The predetermined region may be defined as a region between $\tau_1 \times T_{period}$ and $\tau_2 \times T_{period}$, where $T_{period}$ denotes one cycle time, $\tau_1$ and $\tau_2$ denote arbitrary values, and $\tau_2$ is greater than $\tau_1$.

The processor 120 may calculate a ratio (P2/P1) between an amplitude P1 of a progressive wave component and an amplitude P2 of a first reflection wave component as the TPR feature. The amplitudes P1 and P2 may be amplitude values of the PPG signal that correspond to time values T1 and T2 of a first local minimum point and a second local minimum point.

However, the features are not limited to the above examples, and the processor 120 may extract a combination of values, such as heart rate (HR), time values of each of local minimum points in the second derivative signal, a time value obtained by internally dividing time values of two adjacent local minimum points, amplitude values of the PPG signal that correspond to the time values, cycle of the PPG signal, pulse pressure, etc., as the CO feature or the TPR feature.

Upon extracting the CO feature and/or the TPR feature, the processor 120 may obtain variations in the CO feature and TPR feature compared to a reference CO feature and a reference TPR feature, and may estimate blood pressure by using the obtained variations. In this case, the reference CO feature and the reference TPR feature may refer to features extracted from the PPG signal measured at a reference time in a reference posture. In this case, the reference time may refer to a calibration time when a user is at rest, and the reference posture may be a sitting posture.

$$\Delta f_{CO} = f_{CO,mea} - f_{CO,cal}$$

$$\Delta f_{TPR} = f_{TPR,mea} - f_{TPR,cal} \quad \text{[Equation 2]}$$

Herein, $\Delta f_{CO}$ denotes the variation in CO feature, $\Delta f_{TPR}$ denotes a variation in TPR feature, $f_{CO,mea}$ denotes the CO feature at a time when blood pressure is estimated, $f_{CO,cal}$ denotes the CO feature at the reference time, $f_{TPR,mea}$ denotes the TPR feature at a time when blood pressure is estimated, $f_{TPR,cal}$ denotes the TPR feature at the reference time.

Figure 2:
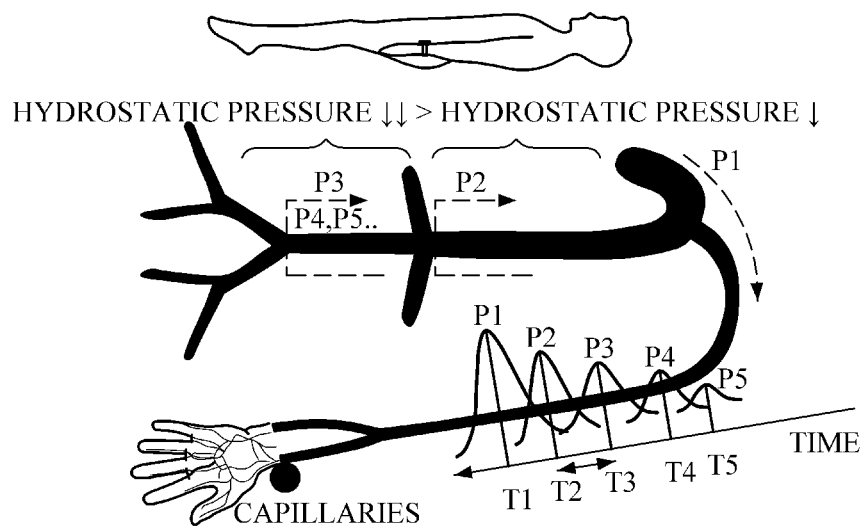
FIG. 2 is a diagram explaining the principle of generating component waveforms of a PPG signal.

FIG. 2 is a diagram explaining the principle of generating component waveforms of a PPG signal.

Referring to FIG. 2, a PPG signal may be generally a summation of a progressive wave P1 propagating from the heart by blood ejection from the left ventricle toward peripheral parts of the body and vascular branching points, and reflection waves P2, P3, P4, and P5 returning from the peripheral parts of the body or the vascular branching points. As described above, the progressive wave P1 is associated with cardiac characteristics, and the reflection waves P2, P3, P4, and P5 are associated with vascular characteristics. Generally, the progressive wave generated by blood ejection from the left ventricle are mainly reflected from the renal arteries and the iliac arteries to generate a first reflection wave P2 and a second reflection wave P3. As illustrated herein, when a user changes to the supine position (e.g., during sleep), hydrostatic pressure decreases in the renal arteries and the iliac arteries. The decrease in the hydrostatic pressure leads to a change in waveform even when no blood pressure change occurs in the aorta adjacent to the heart, thereby causing a change in cardiovascular feature associated with blood pressure.

Once the sensor 110 measures the PPG signal, the processor 120 may detect a measurement posture of the PPG signal. By using two different waveform components of the PPG signal, the processor 120 may determine whether a user's posture during measurement of the PPG signal is the supine posture (during sleep). For example, the processor 120 may obtain feature values of the two waveform components, and may determine the PPG signal measurement posture based on a difference between the obtained feature values of the two waveform components. In this case, the feature values may be time values, but are not limited thereto. Further, the two waveform components may be the first reflection wave component and the second reflection wave component, and a time of the first reflection wave component and a time of the second reflection wave component may be obtained based on second and third local minimum points which respectively appear second and third in the second derivative signal of the PPG signal. For example, the processor 120 may obtain a time of an internally dividing point (e.g., middle point) between times of local maximum points, which appear on both sides of the second local minimum point, and a time of an internally dividing point (e.g., middle point) between times of local maximum points, which appear on both sides of the third local minimum point, as the time of the first reflection wave component and the time of the second reflection wave component, respectively. In another example, the processor 120 may obtain a time of the second local minimum point and a time of the third local minimum point as the time of the first reflection wave component and the time of the second reflection wave component, respectively. However, the feature values are not limited thereto.

Upon obtaining a difference between the feature values of the two waveform components, the processor 120 may obtain a variation in the difference compared a difference between feature values of two waveform components obtained at the reference time in the reference posture. The following Equation 3 is an example of obtaining a variation from a time interval between the two waveform components obtained at the reference time in the reference posture.

$$\Delta(T_3-T_2)=(T_3-T_2)_{mea}-(T_3-T_2)_{cal} \quad \text{[Equation 3]}$$

Herein, $\Delta(T_3-T_2)$ denotes the variation in the time interval between the two waveform components measured at two different times, namely a reference time (e.g., a calibration time) and a blood pressure estimation time, $(T_3-T_2)_{mea}$ denotes the time interval between the two waveform components at the blood pressure estimation time, and $(T_3-T_2)_{cal}$ denotes the time interval between the two waveform components at the reference time.

Upon obtaining the variation in the feature values of the two waveform components, the processor 120 may compare the variation with a threshold value, and if the variation is greater than or equal to the threshold value, the processor 120 may determine that a user's measurement posture is the supine posture, and if not, the processor 120 may determine that the user's measurement posture is the reference posture. Upon determining that the measurement posture is the reference posture, the processor 120 may estimate blood pressure by using per se the CO feature variation ($\Delta f_{CO}$) and the TPR feature variation ($\Delta f_{TPR}$) which are obtained using Equation 2, and upon determining that the measurement posture is the supine posture, the processor 120 may correct the CO feature variation ($\Delta f_{CO}$) and the TPR feature variation ($\Delta f_{TPR}$) and may estimate blood pressure by using the corrected variations.

For example, upon determining that a user's measurement posture is the supine posture, the processor 120 may subtract a correction value for a change in posture from the CO feature variation before correction and the TPR feature variation before correction. In this case, the correction value may be predefined as various values.

For example, the processor 120 may define a value, indicating a change in waveform of the PPG signal during blood pressure estimation, as the correction value. If there is a large variation in cardiovascular feature due to a change in intravascular pressure (hydrostatic pressure+reference blood pressure), the waveform may change significantly even due to a change in hydrostatic pressure. Accordingly, a value, obtained by multiplying an absolute value of the feature variation before correction by a predetermined coefficient, may be defined as the correction value that indicates the change in waveform of the PPG signal, as shown in the following Equation 4.

$$\Delta f_{co} = \Delta f_{co,pre} - g_{coef} \times |\Delta f_{co,pre}|$$

$$\Delta f_{TPR} = \Delta f_{TPR,pre} - g_{coef} \times |\Delta f_{TPR,pre}| \quad \text{[Equation 4]}$$

Herein, $g_{coef}$ denotes the predetermined coefficient and may be, for example, a value less than or equal to 1. The coefficient may be adjusted to various values for improving device performance and may be defined differently for each of the CO feature and the TPR feature.

In another example, a value associated with a change in a user's aortic characteristics may be defined as the correction value. Generally, even in a similar hydrostatic pressure change, the change in waveform may be proportional to a degree of change in vascular characteristics of the central artery, i.e., elasticity of the aorta, or may be inversely proportional to stiffness thereof. Accordingly, as shown in the following Equation 5, a value that is proportional to the reciprocal of the ratio (P2/P1) between the amplitude P1 of the progressive wave component and the amplitude P2 of the first reflection wave component, which are measured at the reference time in the reference posture, as the correction value associated with a user's arterial elasticity.

$$\Delta f_{co} = \Delta f_{co,pre} - 0.08 \times \frac{1}{(P2/P1)_{cal}} \quad \text{[Equation 5]}$$

$$\Delta f_{TPR} = \Delta f_{TPR,pre} - 0.08 \times \frac{1}{(P2/P1)_{cal}}$$

The value of 0.08 is provided here is just an example, and can be adjusted based on individual user characteristics. In addition, the CO feature and the TPR feature may have different values, and $(P2/P1)_{cal}$ denotes the ratio between the amplitude of the progressive wave component and the amplitude of the first reflection wave component which are measured at the reference time in the reference posture.

In another example, a fixed correction value may be defined and commonly applied to a plurality of users. Hydrostatic pressure around the aorta is relatively consistent among individuals due to a vascular length of the central aorta and the little effect of a posture change. Accordingly, assuming that there is little difference in variation of cardiovascular characteristics due to a posture change, a predetermined arbitrary constant value may be defined as the correction value, as shown in the following Equation 6.

$$\Delta f_{co} = \Delta f_{co,pre} - f_{co,off}$$

$$\Delta f_{TPR} = \Delta f_{TPR,pre} - f_{TPR,off} \quad \text{[Equation 6]}$$

Herein, $\Delta f_{co,pre}$ denotes the CO feature variation before correction, $\Delta f_{TPR,pre}$ denotes the TPR feature variation before correction, $f_{co,off}$ denotes a fixed constant value for the CO feature, and $f_{TPR,off}$ denotes a fixed constant value for the TPR feature. In this case, the fixed constant value may be defined as about 0.1 and may be defined differently for each of the CO feature and the TPR feature.

The processor 120 may estimate blood pressure by using the CO feature variation and the TPR feature variation after correcting for variations in the supine posture. The CO feature variation and the TPR feature variation may refer to variations after correction when the measurement posture is the supine posture. The processor 120 may linearly combine the CO feature variation and the TPR feature variation as shown in the following Equation 7, and may estimate blood pressure by inputting the combined value to a blood pressure estimation model as shown in the following Equation 8. The blood pressure estimation model is not limited thereto, and may be a neural network-based model trained by regression analysis, deep learning, and the like.

$$\Delta f_{comb} = w1 \times \Delta f_{co} + w2 \times \Delta f_{TPR} \quad \text{[Equation 7]}$$

Herein, $\Delta f_{comb}$ denotes a value obtained by combining the CO feature variation and the TPR feature variation, and w1 and w2 denote coefficients predefined for the respective feature variations.

$$BP = f(\Delta f_{comb}) + BP_{off} \quad \text{[Equation 8]}$$

Herein, $f(\Delta f_{comb})$ denotes a function for the value obtained by combining the feature variations and is defined in the form of various functions, and may be a function for multiplying a predetermined scaling factor. $BP_{off}$ denotes a reference blood pressure value measured at the reference time by a cuff sphygmomanometer and the like.

The processor 120 may compare blood pressure, estimated during sleep in the supine posture, with blood pressure estimated in the reference posture. Based on this comparison, the processor 120 may predict a variety of information related to cardiovascular diseases. For example, if a blood pressure level during sleep does not fall by a threshold value or more compared to a blood pressure level during non-sleep, or if the blood pressure level during sleep is not within a normal blood pressure range, the processor 120 may guide a user on the risk of developing cardiovascular diseases, such as thrombosis, orthostatic hypotension, and the like.

Figure 3:
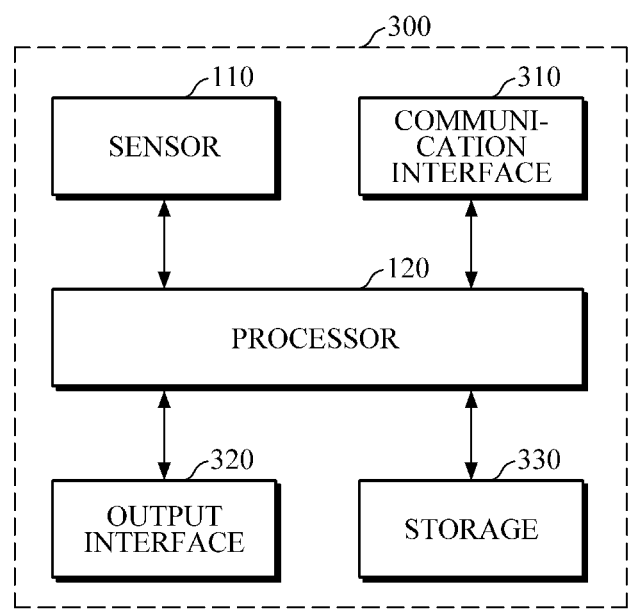
FIG. 3 is a block diagram illustrating an apparatus for estimating blood pressure according to another embodiment of the present disclosure.
Figure 4A:
FIGS. 4A, 4B, and 4C are diagrams illustrating an example of providing information related to estimating blood pressure by an electronic device.
Figure 4B:
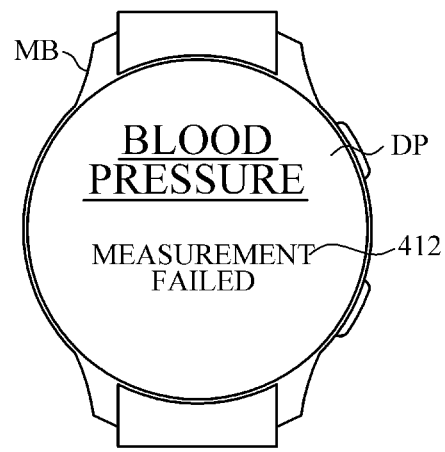
Figure 4C:
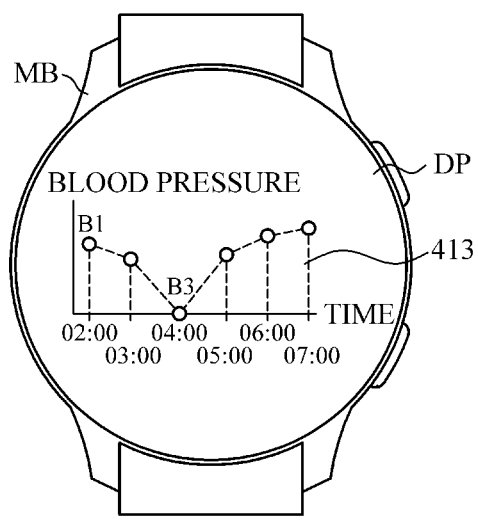

FIG. 3 is a block diagram illustrating an apparatus for estimating blood pressure according to another embodiment of the present disclosure. FIGS. 4A to 4C are diagrams illustrating an example of providing information related to estimating blood pressure by an apparatus for estimating blood pressure.

Referring to FIG. 3, an apparatus 300 for estimating blood pressure includes the sensor 110, the processor 120, a communication interface 310, an output interface 320, and a storage 330. The sensor 110 and the processor 120 are described in detail above, such that a description thereof will be omitted below.

The communication interface 310 may be electrically connected to the processor 120 and may transmit and receive data with another electronic device under the control of the processor 120. In this case, the data may include reference blood pressure, blood pressure estimation models, estimated blood pressure values, and the like. Examples of another electronic device may include a blood pressure measuring device such as a cuff sphygmomanometer, a smartphone, a tablet PC, a desktop computer, a laptop computer, and the like. However, the electronic device is not limited thereto. In this case, the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, and 5G communications, and the like. However, the communication techniques are not limited thereto.

The output interface 320 may output processing results of the sensor 110 and/or the processor 120 and may provide the results to a user. The output interface 320 may provide the user with information by various visual/non-visual methods using a visual output module such as a display, an audio output module such as a speaker, or a haptic module using vibrations, tactile sensation, and the like.

For example, referring to FIGS. 4A and 4B, the output interface 320 may display a blood pressure estimation result 411 on a display DP disposed on a main body MB of the apparatus 300 for estimating blood pressure. The output interface 320 may output a text, such as "blood pressure measured during sleep." If the sensor 110 is not in normal contact with an object during sleep, such that no PPG signal is measured, or if it is determined that a quality of the PPG signal is abnormal, the output interface 320 may output a text 412, such as "measurement failed," as illustrated in FIG. 4B. In addition, if the PPG signal is measured every hour during sleep as illustrated in FIG. 4C, the output interface 320 may display a measurement result in a visual graph 413. In this case, if a user selects a graphic object B1 at a specific time on the graph 413, the output interface 320 may display a blood pressure estimation result at a corresponding time (e.g., 2:00 am.) as illustrated in FIG. 4A. In addition, if the user selects a graphic object B3, the output interface 320 may display information about the measurement failure at a corresponding time, e.g., 4:00 a.m., as illustrated in FIG. 4B. However, the output interface 320 is not limited thereto.

The storage 330 may store data necessary for the sensor 110 and/or the processor 120, and/or the processing results of the sensor 110 and/or the processor 120. For example, the storage 330 may store a blood pressure estimation model, a threshold value, user characteristics (e.g., gender, age, health condition, etc.), a bio-signal, an estimated blood pressure value, a reference feature at a reference time, a reference blood pressure, and the like. The storage 330 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

FIG. 5 is a flowchart illustrating a method of estimating blood pressure according to an embodiment of the present disclosure. The method of estimating blood pressure in FIG. 5 may be performed by the aforementioned apparatuses 100 and 300 for estimating blood pressure.

First, the apparatus for estimating blood pressure may measure a PPG signal in operation 511. In this case, the apparatus for estimating blood pressure may perform preprocessing, such as filtering the input PPG signal, extracting a representative waveform, and the like.

Then, the apparatus for estimating blood pressure may extract a cardiovascular feature from the PPG signal in operation 512. The cardiovascular feature may include a CO feature and a TPR feature which are associated with blood pressure. The CO feature may represent a ratio between a maximum amplitude value in a systolic region and a waveform area. The TPR feature may represent a ratio between an amplitude of a progressive wave component and an amplitude of a first reflection wave component.

Subsequently, the apparatus for estimating blood pressure may obtain a first variation in the cardiovascular feature (e.g., a variation $\Delta f_{CO}$ in the CO feature, and a variation $\Delta f_{TPR}$ in the TPR feature), extracted in operation 512, compared to a reference feature obtained from a PPG signal measured at a reference time in a reference posture (e.g., a sitting posture, or a lying down posture) in operation 513.

Next, the apparatus for estimating blood pressure may extract times Ti and Tj of two waveform components of the PPG signal in operation 514. In this case, the two waveform components may be a first reflection wave and a second reflection wave, and as described above, times obtained based on second and third local minimum points, which appear second and third in a second derivative signal, may be obtained as a time of the first reflection wave and a time of the second reflection wave, respectively.

Then, the apparatus for estimating blood pressure may obtain a time interval (Tj−Ti) between the two waveform components and may obtain a variation (Δ(Tj−Ti)) in the time interval (Tj−Ti) between the two waveform components compared to a reference time interval between two waveform components obtained at the reference time in operation 515.

Subsequently, the apparatus for estimating blood pressure may compare the variation, obtained in operation 515, with a threshold value Tth in operation 516.

Upon comparison, if the variation is less than the threshold value, the apparatus for estimating blood pressure may estimate blood pressure in operation 517 by using the first variation obtained in operation 513.

Upon comparison, if the variation is greater than the threshold value, the apparatus for estimating blood pressure may obtain a second variation in operation 518 by correcting the first variation. For example, by using, as a correction value, an arbitrary fixed value (e.g., $c1_{offset}$ and $c2_{offset}$) which may be commonly applied to all users, a value (e.g., $f1_{subject}$ and $f2_{subject}$) associated with vascular compliance of each individual user, or a value (e.g., $g1_{coeff}*|\Delta f_{co}|$ and $g2_{coeff}*|\Delta f_{TPR}|$) obtained by considering a change in waveform of the PPG signal measured in operation 511, the apparatus for estimating blood pressure may obtain the second variation (e.g., ($\Delta f_{CO}-c1_{offset}$, $\Delta f_{TPR}-c2_{offset}$), ($\Delta f_{CO}-f1_{subject}$, $\Delta f_{TPR}-f2_{subject}$), or ($\Delta f_{CO}-g1_{coeff}*|\Delta f_{co}|$, $\Delta f_{TPR}-g2_{coeff}*|\Delta f_{TPR}|$)) by subtracting the correction value from the first variation.

Next, the apparatus for estimating blood pressure may estimate blood pressure by using the second variation in operation 519.

Then, the apparatus for estimating blood pressure may output the estimated blood pressure value in operation 520. For example, the apparatus for estimating blood pressure may output an estimated blood pressure value at a specific time point or a trend graph of estimated blood pressure values over a predetermined period of time, etc., and if an estimated blood pressure value is not within a (predetermined) normal range, the apparatus for estimating blood pressure may output warning information.

Figure 6:
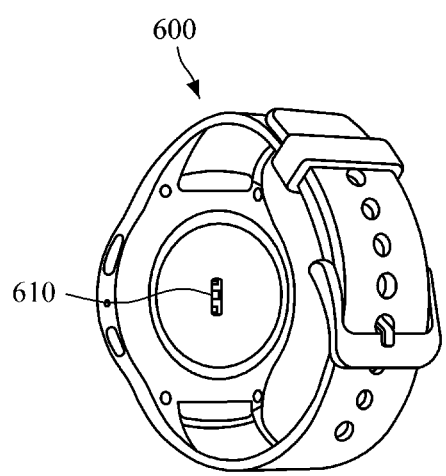
FIGS. 6 to 8 are diagrams illustrating examples of various structures of an electronic device including an apparatus for estimating blood pressure.
Figure 7:
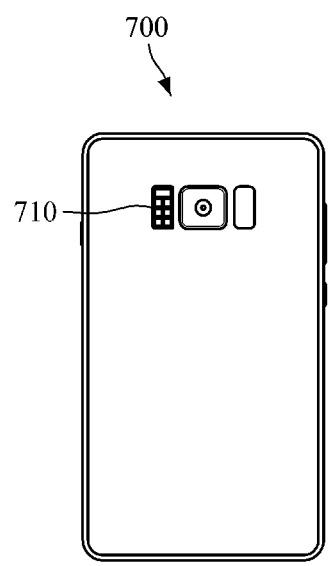
Figure 8:
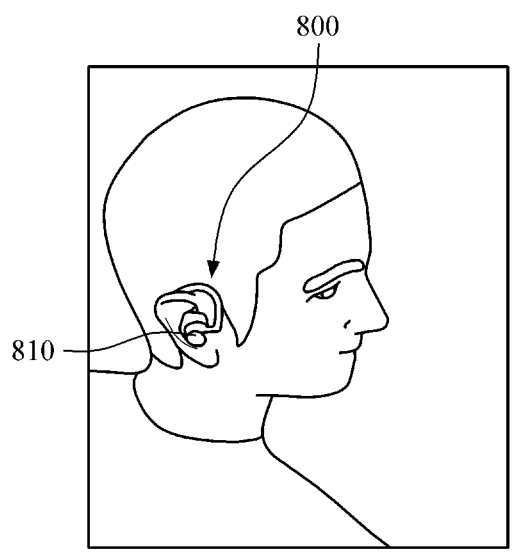

FIGS. 6 to 8 are diagrams illustrating examples of various structures of an electronic device including an apparatus for estimating blood pressure.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

The electronic device may include a sensor device, a processor, an input device, a communication module, a camera module, an output device, a storage device, and a power module. All the components of the electronic device may be integrally mounted in a specific device or may be distributed in two or more devices. The sensor device may include the sensor 110 of the apparatuses 100 and 300 for estimating blood pressure, and may further include an additional sensor, such as a gyro sensor, a Global Positioning System (GPS), and the like.

The processor may execute programs, stored in the storage device, to control components connected to the processor, and may perform various data processing or computation, including estimation of bio-information. The processor may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The input device may receive a command and/or data to be used by each component of the electronic device, from a user and the like. The input device may include, for example, a microphone, a mouse, a keyboard, or a digital pen (e.g., a stylus pen, etc.).

The communication module may support establishment of a direct (e.g., wired) communication channel and/or a wireless communication channel between the electronic device and other electronic device, a server, or the sensor device within a network environment, and performing of communication via the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 700 in a communication network by using subscriber information (e.g., international mobile subscriber identity (IMSI), etc.) stored in a subscriber identification module.

The camera module may capture still images or moving images. The camera module may include a lens assembly having one or more lenses, image sensors, image signal processors, and/or flashes. The lens assembly included in the camera module may collect light emanating from a subject to be imaged.

The output device may visually/non-visually output data generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device may store operating conditions required for operating the sensor device, and various data required for other components of the electronic device. The various data may include, for example, input data and/or output data for software and instructions related thereto. The storage device may include a volatile memory and/or a non-volatile memory.

The power module may manage power supplied to the electronic device. The power module may be implemented as part of, for example, a power management integrated circuit (PMIC). The power module may include a battery, which may include a primary cell which is not rechargeable, a secondary cell which is rechargeable, and/or a fuel cell.

Referring to FIG. 6, the electronic device may be implemented as a wristwatch wearable device 600, and may include a main body and a wrist strap. A display is provided on a front surface of the main body, and may display various application screens, including time information, received message information, and the like. A sensor device 610 may be disposed on a rear surface of the main body.

Referring to FIG. 7, the electronic device may be implemented as a mobile device 700 such as a smartphone. The mobile device 700 may include a housing and a display panel. The housing may form an exterior of the mobile device 700. The housing has a first surface, on which a display panel and a cover glass may be disposed sequentially, and the display panel may be exposed to the outside through the cover glass. A sensor device 710, a camera module and/or an infrared sensor, and the like may be disposed on a second surface of the housing. The processor and various other components may be disposed in the housing.

Referring to FIG. 8, the electronic device may be implemented as an ear-wearable device 800. The ear-wearable device 800 may include a main body and an ear strap. A user may wear the ear-wearable device 800 by hanging the ear strap on the auricle. The ear strap may be omitted depending on a shape of the ear-wearable device 800. The main body may be inserted into the external auditory meatus. A sensor device 810 and a processor may be mounted in the main body, and blood pressure may be estimated by using a PPG signal measured by the sensor device 810. Alternatively, the ear-wearable device 800 may estimate blood pressure by interworking with an external device. For example, the PPG signal, measured by the sensor device 810 of the ear-wearable device 800, may be transmitted to an external device, e.g., a smartphone, a tablet PC, etc., through a communication module provided in the main body, so that a processor of the external device may estimate blood pressure, and the estimated blood pressure value may be visually output to a display of the external device, and may be output through a sound output module provided in the main body of the ear-wearable device 800.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
   a photoplethysmogram (PPG) sensor configured to measure a PPG signal from a user; and a processor configured to:
extract a cardiovascular feature from the PPG signal;
calculate a first variation in the extracted cardiovascular feature compared to a reference cardiovascular feature measured at a reference time;
determine a measurement posture of the PPG signal based on a time interval between two waveform components of the PPG signal;
in response to the measurement posture corresponding to a reference posture, estimate the blood pressure based on the first variation; and
in response to the measurement posture not corresponding to the reference posture, calculate a correction value by multiplying an absolute value of the first variation by a predetermined coefficient, obtain a second variation by subtracting the correction value from the first variation, and estimate blood pressure based on the second variation.

2. The apparatus of claim 1, wherein the PPG sensor comprises:
a light source configured to emit light to the user; and
a detector configured to detect light scattered or reflected from the user.

3. The apparatus of claim 1, wherein the processor is further configured to:
obtain a variation in a difference between feature values of the two waveform components compared to a difference between feature values of two waveform components obtained at the reference time in the reference posture; and
in response to the obtained variation being greater than or equal to a threshold value, determine that the measurement posture does not correspond to the reference posture.

4. The apparatus of claim 3, wherein the processor is further configured to:
obtain a second derivative signal of the PPG signal; and
obtains a time of a second local minimum point of the second derivative signal, and a time of a third local minimum point of the second derivative signal, as the feature values of the two waveform components.

5. The apparatus of claim 1, wherein the cardiovascular feature comprises a cardiac output (CO) feature associated with CO and a total peripheral resistance (TPR) feature associated with TPR.

6. The apparatus of claim 5, wherein:
the CO feature comprises a ratio between a maximum amplitude value of the PPG signal and an area of a predetermined region of the PPG signal; and
the TPR feature comprises a ratio between an amplitude value of a first reflection wave component and an amplitude value of a progressive wave component of the PPG signal.

7. The apparatus of claim 5, wherein the processor is further configured to:
in response to the measurement posture of the PPG signal corresponding to the reference posture, combine the first variation in the CO feature and the first variation in the TPR feature, and estimate the blood pressure based on a combination of the first variation in the CO feature and the first variation in the TPR feature; and
in response to the measurement posture not corresponding to the reference posture, combine the second variation in the CO feature and the second variation in the TPR feature, and estimate the blood pressure based on a combination of the second variation in the CO feature and the second variation in the TPR feature.

8. The apparatus of claim 7, wherein the processor is further configured to:
in response to the measurement posture of the PPG signal corresponding to the reference posture, estimate the blood pressure by inputting the combination of the first variation in the CO feature and the first variation in the TPR feature, and a reference blood pressure to a blood pressure estimation model; and
in response to the measurement posture not corresponding to the reference posture, estimate the blood pressure by inputting the combination of the second variation in the CO feature and the second variation in the TPR feature, and the reference blood pressure to the blood pressure estimation model.

9. A method of estimating blood pressure, the method comprising:
measuring a photoplethysmogram (PPG) signal from a user;
extracting a cardiovascular feature from the PPG signal;
calculating a first variation in the extracted cardiovascular feature compared to a reference cardiovascular feature measured at a reference time;
determining a measurement posture of the PPG signal based on a time interval between two waveform components of the PPG signal;
in response to the measurement posture corresponding to a reference posture, estimating the blood pressure based on the first variation; and
in response to the measurement posture not corresponding to the reference posture, calculating a correction value by multiplying an absolute value of the first variation by a predetermined coefficient, obtaining a second variation by subtracting the correction value from the first variation, and estimating blood pressure based on the obtained second variation.

10. The method of claim 9, wherein the determining of the measurement posture comprises:
obtaining a variation in a difference between feature values of the two waveform components compared to a difference between feature values of two waveform components obtained at the reference time in the reference posture; and
in response to the obtained variation being greater than or equal to a threshold value, determining that the measurement posture does not correspond to the reference posture.

11. The method of claim 10, wherein the determining of the measurement posture comprises:
obtaining a second derivative signal of the PPG signal; and
obtaining a time of a second local minimum point of the second derivative signal, and a time of a third local minimum point of the second derivative signal, as the feature values of the two waveform components.

12. The method of claim 9, wherein the cardiovascular feature comprises a cardiac output (CO) feature associated with CO and a total peripheral resistance (TPR) feature associated with TPR.

13. The method of claim 12, wherein:
the CO feature comprises a ratio between a maximum amplitude value of the PPG signal and an area of a predetermined region of the PPG signal; and
the TPR feature comprises a ratio between an amplitude value of a first reflection wave component and an amplitude value of a progressive wave component of the PPG signal.

14. The method of claim 12, wherein the estimating of the blood pressure comprises:
　　in response to the measurement posture of the PPG signal corresponding to the reference posture, combining the first variation in the CO feature and the first variation in the TPR feature, and estimating the blood pressure based on a combination of the first variation in the CO feature and the first variation in the TPR feature; and
　　in response to the measurement posture not corresponding to the reference posture, combining the second variation in the CO feature and the second variation in the TPR feature, and estimating the blood pressure based on a combination of the second variation in the CO feature and the second variation in the TPR feature.

* * * * *